(12) United States Patent
Raguse et al.

(10) Patent No.: US 9,874,541 B2
(45) Date of Patent: Jan. 23, 2018

(54) CHEMIRESISTOR SENSOR

(71) Applicant: Commonwealth Scientific and Industrial Research Organisation, Campbell, Australian Capital Territory (AU)

(72) Inventors: Burkhard Raguse, Gordon (AU); Edith Chow, Ryde (AU)

(73) Assignee: Commonwealth Scientific and Industrial Research Organization (AU)

( * ) Notice: Subject to any disclaimer, the term of this patent is extended or adjusted under 35 U.S.C. 154(b) by 20 days.

(21) Appl. No.: 14/778,305

(22) PCT Filed: Mar. 19, 2014

(86) PCT No.: PCT/AU2014/000295
§ 371 (c)(1),
(2) Date: Sep. 18, 2015

(87) PCT Pub. No.: WO2014/146171
PCT Pub. Date: Sep. 25, 2014

(65) Prior Publication Data
US 2016/0282302 A1   Sep. 29, 2016

(30) Foreign Application Priority Data
Mar. 21, 2013   (AU) .................... 2013900988

(51) Int. Cl.
*G01N 27/04* (2006.01)
*G01N 27/12* (2006.01)
(Continued)

(52) U.S. Cl.
CPC ......... *G01N 27/4146* (2013.01); *G01N 27/04* (2013.01); *G01N 27/128* (2013.01);
(Continued)

(58) Field of Classification Search
CPC ...... G01N 27/04; G01N 27/12; G01N 27/126; G01N 27/127; G01N 27/128;
(Continued)

(56) References Cited

U.S. PATENT DOCUMENTS

| 7,189,360 B1* | 3/2007 | Ho ................. G01N 27/126 29/592.1 |
| 8,940,235 B2* | 1/2015 | Wu ................. H01L 51/0036 257/40 |

(Continued)

FOREIGN PATENT DOCUMENTS

WO   2008092210 A1   8/2008

OTHER PUBLICATIONS

Lange et al. Analytica Chimica Acta, vol. 687, Dec. 11, 2010, pp. 7-11.*

(Continued)

*Primary Examiner* — Maureen Wallenhorst
(74) *Attorney, Agent, or Firm* — Tarolli, Sundheim, Covell & Tummino LLP

(57) ABSTRACT

A sensor is provided with (i) a pair of electrically conducting electrodes on an electrically insulating substrate; (ii) a chemiresistor film in contact with the pair of electrodes, with an impedance that changes in the presence of an ionic analyte; (iii) a gate electrode formed from an electrically conductive material; (iv) a potential generator configured to apply an electrical potential difference between the gate electrode and the chemiresistor film; (v) a controller to selectively control the potential generator to apply an electric potential to the gate electrode relative to the potential of the chemiresistor film; and (vi) a voltage power source adapted to apply a voltage signal between the pair of electrically conducting electrodes to enable measurement of the resistance of the chemiresistor film.

19 Claims, 5 Drawing Sheets

(51) Int. Cl.
*G01N 27/414* (2006.01)
*G01N 33/543* (2006.01)
(52) U.S. Cl.
CPC ... *G01N 33/5438* (2013.01); *G01N 33/54346* (2013.01); *G01N 33/54393* (2013.01); *G01N 27/127* (2013.01)
(58) Field of Classification Search
CPC ......... G01N 27/4146; G01N 33/54346; G01N 33/5438; G01N 33/54393
USPC ............... 436/149, 150, 151, 73, 80, 84; 422/82.01, 82.02
See application file for complete search history.

(56) References Cited

U.S. PATENT DOCUMENTS

| | | | |
|---|---|---|---|
| 8,951,473 B2* | 2/2015 | Wang | B82Y 15/00 422/68.1 |
| 2010/0276302 A1* | 11/2010 | Raguse | G01N 27/127 205/775 |
| 2012/0186987 A1 | 7/2012 | Mirsky et al. | |

OTHER PUBLICATIONS

Raguse et al. Analytical Chemistry, vol. 79, 2007, pp. 7333-7339.*
International Search Report to corresponding International Application No. PCT/AU2014/000295, dated Jun. 10, 2014, 3 pages.

* cited by examiner

CHEMIRESISTOR SENSOR

CROSS-REFERENCE TO RELATED APPLICATIONS

The present application is a U.S. National Stage under 35 USC 371 patent application, claiming priority to Serial No. PCT/AU2014/000295, filed on 19 Mar. 2014, which claims priority from Australian Provisional Patent Application No 2013900988 filed on 21 Mar. 2013, the entirety of both which is incorporated herein by reference.

TECHNICAL FIELD

The present invention relates to a chemical sensor for sensing properties of a fluid, in particular to a sensor that utilise chemiresistor materials that are capable of detecting ionic analytes in a liquid environment.

BACKGROUND

Chemiresistive materials are a class of material that change their electrical resistance in response to an interaction with a chemical. In particular, chemiresistive materials commonly consist of a mixture of conductive particular matter coated or suspended in an essentially non-conductive material. The ratio of conductive to non-conductive material is such that the materials conductance or resistance can be measured using standard techniques. Generally the non-conductive material consists of, but is not limited to, an organic material such as a polymer or a self-assembled monolayer. It is generally accepted by those skilled in the art that these chemiresistive materials function through adsorption of chemical species into the organic material. This adsorption causes a swelling of the organic material, which subsequently increases the distance between the conductive particles, thereby causing an increase in the chemiresistive materials resistance.

Chemiresistors and arrays of chemiresistors for determining levels of analytes in the gas or liquid-phase are well-established in the art by measuring resistance changes of chemiresistive materials in the presence of particular analytes. One method of realising such a chemiresistor is to prepare thin films of gold nanoparticles that are coated with organic molecules (the chemiresistive material), and with two electrodes on either end. Wohltjen and Snow (Anal. Chem., 1998, 70, 2856) teach that the exposure of thin films of gold nanoparticle-based materials to organic vapours such as toluene in nitrogen carrier gas result in reversible film swelling. The swelling causes the conducting particles to move further apart which leads to an increase in the resistance of the chemiresistor.

A variety of materials can also be used as the sensing element for chemiresistors. For instance, carbon black can be mixed with a conducting or non-conducting polymer (Lonergan et al., Chem Mater., 1996, 8, 2298; Doleman et al, Anal. Chem., 1998, 70, 4177; Sotzing et at, Chem Mater., 2000, 12, 593) and deposited between two electrodes to form a chemiresistor for detecting gases or vapour. Moreover, graphene (Schedin et al., Nat. Mater., 2007, 6, 652) and carbon nanotubes (Wang et al., J. Am. Chem. Soc., 2008, 46, 8394) have attracted interest in recent years as materials that can change their conductivity in the presence of a chemical species. Such chemiresistors have been exclusively used for gas or vapour-phase detection of analytes.

WO 2008/092210 A1 to Raguse et al, teaches the use of chemiresistors in an electrolyte solution. To realise such a chemiresistor, the electrodes and chemiresistive materials are designed so that the chemiresistor film impedance is lower than the impedance due to the double layer capacitance of the total electrode surface in contact with the electrolyte solution. When exposed to toluene, dichloromethane or ethanol dissolved in the electrolyte solution, the nanoparticle film increases in resistance.

Raguse et al. (WO 2008/092210 A1 and J. Phys Chem C, 2009, 113(34), 15390) further teaches that the degree of interaction between an organic molecule dissolved in aqueous solution and the nanoparticle film is proportional to the partition coefficient between the two, and for hexanethiol-functionalized gold nanoparticles, mirrors the well-known octanol-water partition coefficient. However, these results indicate that ionically charged molecules, which have small water-octanol partition coefficients (i.e. which have a relatively high water solubility compared to non-polar, uncharged organic molecules) will partition into the chemiresistor film only poorly. Such weak interactions between ionically charged molecules and the chemiresistor materials would lead to only small changes in the chemiresistor resistance in the presence of such charged molecules. Thus there exists a need to improve the ability of chemiresistor sensors that function in electrolyte solutions to interact with ionic analytes in order to improve sensitivity and selectivity towards said charged analytes.

There are a number of applications where it would be advantageous to increase the interaction between chemiresistor materials and charged molecules dissolved in electrolyte solution. For instance, a large number of analytes of interest to the pharmaceutical, environmental or biomedical industries are charged molecules. These include, but are not limited to, various drugs, pesticides, herbicides, amino acids, peptides, metabolites.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Embodiments of the present invention provide highly sensitive devices and methods for detecting small molecules having a molecular weight of less than about 2,000 daltons. Particular embodiments relate to the detection of small molecules having a molecular weight less than 1,000 daltons, more particularly of between about 50 and 650 daltons and more particularly of between about 500 and 600 daltons.

In a first aspect, a sensor is provided for measuring the presence or amount of an ionic analyte in an electrolyte solution, said sensor comprising:

(i) two electrically conducting electrodes on an electrically insulating substrate, and separated by a distance L, where L is between 10 nm and 100 µm;

(ii) a chemiresistor film, wherein the impedance of the chemiresistor film changes in the presence of an ionic analyte; and wherein the chemiresistor film is in contact with the electrodes;

(iii) a gate electrode formed from an electrically conductive material;

(iv) a potential generator means configured to apply an electrical potential difference between the gate electrode and the chemiresistor film;

(v) a controller to selectively control the potential generator means to apply either a positive electric potential or a negative electric potential to the gate electrode relative to the potential of the chemiresistor film; and (vi) a voltage means adapted to apply a voltage signal between said pair of electrically conducting electrodes to enable measurement of the resistance of the chemiresistor film.

The sensor may further comprises a device for measuring the resistance of said chemiresistor film under the voltage signal.

In one embodiment, the gate electrode may be formed from gold, platinum, palladium, silver, or carbon. The gate electrode may be an Ag/AgCl gate electrode and the Ag/AgCl gate electrode may be formed from silver that has been chlorided. Preferably, the gate electrode is a gold electrode.

In a second embodiment, the gate electrode comprises a counter electrode and reference electrode combination. The counter electrode may be formed from gold, platinum, palladium, silver or conductive carbon. The reference electrode may be a standard reference electrode such as those commonly used in electrochemistry, for instance Ag/AgCl, non-aqueous Ag/Ag+, mercury/mercurous sulphate, or saturated calomel electrode.

In an embodiment, at least one component of said electrolyte solution is a net positively charged or net negatively charged molecule which possesses an interaction group. The inventors have determined that if said molecule penetrates into the chemiresistor film the interaction group interacts with the organic material of the chemiresistor film resulting in the chemiresistor film changing its resistance.

In an embodiment where a positive potential is applied to the gate electrode relative to the chemiresistive material, net positively charged molecules in solution penetrate into the chemiresistive material. The potential waveform between the gate electrode and the chemiresistive material may be applied by a number of standard methods known to those skilled in the art. These may include pulse, double or multiple pulse, square wave, triangle wave, staircase.

In one embodiment a steady-state potential is applied between the gate electrode and the chemiresistive material. Preferably a steady-state potential in a range between +2000 mV and −2000 mV is applied, more preferably between +1000 mV and −1000 mV and most preferably in the range of between +500 mV to −500 mV.

In a further embodiment a triangular waveform is applied, that is, where the potential is swept linearly with time, the sweep is initiated from a potential $V_0$ between −2000 mV and 2000 mV and swept to an upper vertex potential $V_1$ of 2000 mV and then swept to a lower vertex potential $V_2$ of −2000 mV. The sweep rate may be between 0.1 and 1000 mV/s and the number of cycles one or more. The entire measurement may be performed in the presence of a charged molecule. It is preferred if $V_0$ is 0 mV, $V_1$ is up to +1000 mV, $V_2$ is down to −1000 mV, the sweep rate is between 1 mV/s and 10 mV/s. It is more preferred if $V_0$ is 0 mV, $V_1$ is +500 mV, $V_2$ is −500 mV, sweep rate is 1 mV/s.

In a still further embodiment where a pulse is made, that is, where a constant potential is applied between the gate and the chemiresistive material, and the current is measured over time, it is preferred that the pulse is made at a lower potential $V_1$ for 1 s-60 min, then switched to a higher potential $V_2$ for 1 s-60 min, all in the presence of the charged molecule. It is preferred that $V_1$ is a negative value down to −2000 mV, $V_2$ is a positive value up to +2000 mV, and with each pulse lasting 1 min-10 min. It is more preferred if $V_1$ is 0 mV, and $V_2$ is +500 mV with each pulse lasting 2 min-5 min. It is most preferred if $V_t$ is −500 mV, and $V_2$ is +500 mV with each pulse lasting 2 min-5 min. Preferably in the case where a pulse is made, it is preferred that the potential is held at a single potential between +1 mV and +2000 mV and that the current is recorded in a blank solution for 1 s-60 min, then switched to the charged molecule for 1 s-60 min. More preferably, the exposure duration for each solution is 1 min-10 min and the potential is held between +100 mV and +1000 mV. Most preferably, the exposure duration for each solution is 2 min-5 min and the potential is held at +500 mV.

In the case where one wishes to reverse the resistance of the chemiresistive material, then the solution may be switched back to a blank solution for 1 s-60 min.

The present inventors have determined that for a given concentration of a net positively charged molecule in solution, that by applying an electrical potential difference between the gate electrode and the chemiresistive material, such that the gate electrode is positively charged compared to the chemiresistive material, the amount of change in resistance of the chemiresistive material can be made to increase compared to the amount of resistance change in the absence of an electrical potential difference between the gate electrode and the chemiresistive material.

The present inventors have further determined that by reversing the electrical potential difference between the gate electrode and the chemiresistive material, in the situation described in the preceding paragraph, the resistance change in the chemiresistive material induced by the charged molecule can be essentially reversed.

In an optional embodiment where a negative potential is applied to the gate electrode relative to the chemiresistive material, net negatively charged molecules in solution penetrate into the chemiresistive material.

In one embodiment where a triangular waveform is applied, that is, where the potential is swept linearly with time, it is preferred that the sweep is initiated from a potential $V_0$ between −2000 mV and 2000 mV and swept to a lower vertex potential $V_1$ of −2000 mV and then swept to an upper vertex potential $V_2$ of +2000 mV. The sweep rate is between 0.1 and 1000 mV/s and the number of cycles is greater than 1. The entire measurement is performed in the presence of a charged molecule. It is more preferred if $V_0$ is 0 mV, $V_1$ is down to −1000 mV, $V_2$ is up to +1000 mV, the sweep rate is between 1 mV/s and 10 mV/s. It is most preferred if $V_1$ is −500 mV, $V_2$ is +500 mV, sweep rate is 1 mV/s.

In a further embodiment where a pulse is made, that is, where a constant potential is applied between the gate and the chemiresistive material, and the current is measured over time, it is preferred that the pulse is made at an upper potential $V_1$ for 1 s-60 min, then switched to a lower potential $V_2$ for 1 s-60 min, all in the presence of the charged molecule. It is preferred that $V_1$ is a positive value up to +2000 mV, $V_2$ is a negative value down to −2000 mV, and with each pulse lasting 1 min-10 min. It is more preferred if $V_1$ is 0 mV, and $V_2$ is −500 mV with each pulse lasting 2 min-5 min. It is most preferred if $V_1$ is +500 mV, and $V_2$ is −500 mV with each pulse lasting 2 min-5 min. Preferably in the case where a pulse is made, it is preferred that the potential is held at a single potential between −1 mV and −2000 mV and that the current is recorded in a blank solution for 1 s-60 min, then switched to the charged molecule for 1 s-60 min.

In the case where one wishes to reverse the resistance of the chemiresistive material, then the solution may be switched back to a blank solution for 1 s-60 min.

More preferably, the exposure duration for each solution is 2-10 min and the potential is held between −100 mV and −1000 mV. Most preferably, the exposure duration for each solution is 2-5 min and the potential is held at −500 mV.

The present inventors have further determined that for a given concentration of a net negatively charged molecule in solution, that by applying an electrical potential difference between the gate electrode and the chemiresistive material, such that the gate electrode is negatively charged compared to the chemiresistive material, the amount of change in resistance of the chemiresistive material can be made to increase compared to the amount of resistance change in the absence of an electrical potential difference between the gate electrode and the chemiresistive material.

The present inventors have further determined that by reversing the electrical potential difference between the gate electrode and the chemiresistive material, in the situation described in the preceding paragraph, the resistance change in the chemiresistive material induced by the charged molecule can be essentially reversed.

The pair of electrically conductive electrodes may be made from any material that has a sufficiently high electrical conductivity such that its resistance is small compared to the resistance of the chemiresistor film and such that it is electrochemically inert under the measurement conditions, that is electrochemically inert when immersed in electrolyte for the period of the measurement. Suitable materials may be inert metals such as gold, palladium, platinum, silver, copper, nickel or conductive materials based on conductive carbon such as carbon black, graphene or carbon nanotubes. Preferred electrode materials are gold, silver, palladium and platinum.

In a preferred embodiment, the pair of electrically conductive electrodes are coated with a thin layer of an inert material, the inert material characterised by:
  (a) having a dielectric constant that is less than that of water;
  (b) being at least partially impermeable towards ions; and
  (c) having a thickness less than 2 nanometers.

This thin layer of an inert material has the effect of decreasing the effective double-layer capacitance (Cdl) of the conductive electrode pads exposed to the electrolyte. For instance it is known in the art that while the Cdl of a bare gold surface has values of between 10-40 $\mu F/cm^2$, a gold surface coated with a self-assembled monolayer of hexadecane thiol has a Cdl of 1 $\mu F/cm^2$, i.e. a reduction in the capacitance value of approximately 10, with a concomitant increase in the impedance by a factor of 10.

It is further preferred that this thin layer of an inert material is a self-assembled monolayer formed onto the surface of the gold, silver, palladium or platinum electrode material. Such self-assembled monolayers may be produced from alkane thiols, alkane disulfides, or other sulphur functionalised molecules.

The self-assembled monolayer may include molecules that additionally can be used to anchor the chemiresistive material to the surface of the conductive electrode pads either via physical interactions such as hydrophobic interactions, or by chemically bonding parts of the chemiresistive material to the self-assembled monolayer.

It is preferred that the substrate onto which the electrodes are patterned/fabricated is produced from silicon wafers, preferably with a layer of silicon dioxide grown on the surface, glass, or plastics.

It is further preferred that the surface of the substrate is functionalised such that it can be used to anchor the chemiresistive material to the surface of the inert non-electrically conducting substrate either via physical interactions such as hydrophobic interactions, or by chemically bonding parts of the chemiresistive material to the self-assembled monolayer.

In an embodiment the ac impedance of the chemiresistive material is determined by impedance spectroscopy at a single frequency or at multiple frequencies. Standard apparatus may be deployed that uses sine waves or pulse methods to determine the low frequency characteristics of the sensor. Preferably ac impedance spectroscopy is used to determine the impedance of the sensor at low frequencies, preferably below 100 Hz to dc, more preferably between 10 Hz and 0.1 Hz, most preferably at 1 Hz.

At the preferred low frequency used to measure the resistance characteristics of the sensor it is preferred that the impedance of the electrically conductive electrode pads in electrolyte solution, but in the absence of the chemiresistor thin film, is twice as large as that when the chemiresistor thin film is deposited across the electrodes, more preferably 5 times larger, most preferably more than 0 times larger.

Preferably the amplitude of the applied voltage of the chemiresistive material is between 10 mV and 500 mV. More preferably the applied voltage is between 20 mV and 200 mV. Most preferably the applied voltage is between 50 mV and 100 mV.

In another embodiment, an array of chemiresistor sensors, comprising at least two chemiresistor sensors, preferably a plurality of devices according to the present invention are made; wherein the individual sensors differ from each other in the type of conductive and/or non-conductive material. By using appropriate chemometric and pattern recognition software known to those skilled in the art, such artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DF A), linear discriminant analysis (LDA), random forest (RF), cluster analysis, and nearest neighbour, different charged molecules can be identified and quantified, based on the different response patterns of the sensors in the array.

In a second aspect, a method is provided for measuring the presence or amount of an ionic analyte in an electrolyte solution using a sensor according to the first aspect or any one of its embodiments, the method comprising:
  (i) contacting the chemiresistive material with an electrolyte solution;
  (ii) applying an electric potential difference between the gate electrode and the chemiresistive material; and
  (iii) measuring the change in the resistance of the chemiresistive material.

The method may further comprise the step of comparing the value of the measurement in step (iii) with measurement(s) of the change in the resistance of the chemiresistive material in the presence of said ionic analyte of one or more known concentrations to thereby determine the amount of ionic analyte in said electrolyte solution.

In a third aspect, a method is provided for modulating the electrical resistance of a chemiresistive material using a sensor according to the first aspect or any one of its embodiments, the method comprising:

(i) contacting the chemiresistive material and the gate electrode with an electrolyte solution;

(ii) applying an electric potential difference between the gate electrode and the chemiresistive material;

(iii) selectively charging the gate electrode with a net positive charge or a net negative charge; and (iv) measuring the change in the resistance of the chemiresistive material.

In one embodiment of the third aspect it is preferred that the charged analyte molecule comprises one or more positive charges (P), such that overall the charged analyte molecule has a net positive charge, and an interaction group (F) of the following structure: P---F; where the interaction group (F) is an organic functional group and said organic functional group comprises one or more chemical moieties capable of physically or chemically binding to the chemiresistive material. In a further embodiment, said interaction group (F) contains as part of its structure, a hydrophobic group such as a hydrocarbon-containing moiety. In the context of the present invention a hydrocarbon-containing moiety is defined as an organic group that is part of an organic molecular structure that contains at least one methylene group.

Such hydrocarbon-containing moieties may additionally include, but are not limited to, hydrophobic moieties such as cyclic or acyclic alkanes, including linear and branched alkanes, cyclic or acyclic alkenes, alkynes, aromatic groups, polyaromatic groups, oxygen-containing heterocyclic groups, nitrogen containing heterocyclic groups, sulphur-containing heterocyclic groups, fluorinated-, chlorinated-, brominated-, iodinated alkanes or aromatic groups, nitroaromatic groups, ethers such as methyl ethers, ethyl ethers, propyl ethers, butyl ethers, pentyl ethers, hexyl ethers and other linear and branched hydrocarbons that contain ether groups.

In a further embodiment, said interacting group (F) contains as part of its structure groups capable of forming hydrogen bonds. Said interacting group (F) may contain as part of its structure groups capable of forming hydrogen bonds such as hydroxyl, amine, carboxylic acid, ester, or ether groups; basic groups such as amines; organic acidic groups such as carboxylic acids, sulfonic acids, boronic acids or phosphonic acids. The chemiresistive material may also contain groups capable of forming hydrogen bonds.

The net positively charged component (P) may comprise at least one organic cationic group. Preferably such a cationic group (P) is a positively charged primary ammonium, secondary ammonium, tertiary ammonium, quaternary ammonium, pyridinium, positively-charged nitrogen-containing heterocycle, or phosphonium group. The charged molecule may additionally contain one or more negatively charged groups so long as the net charge is positive.

In another preferred embodiment the charged analyte molecule may comprise one or more negative charges (N), such that overall the charged analyte molecule has a net negative charge, and an interaction group (F) of the following structure: N---F; where the interaction group (F) is an organic functional group and said organic functional group comprises one or more chemical moieties capable of physically or chemically binding to the chemiresistive material. In one preferred embodiment, said interaction group (F) contains as part of its structure, a hydrophobic group such as a hydrocarbon-containing moiety.

In the context of the present invention a hydrocarbon-containing moiety is defined as an organic group that is part of an organic molecular structure that contains at least one methylene group.

Such hydrocarbon-containing moieties may additionally include, but are not limited to, hydrophobic moieties such as cyclic or acyclic alkanes, including linear and branched alkanes, cyclic or acyclic alkenes, alkynes, aromatic groups, polyaromatic groups, oxygen-containing heterocyclic groups, nitrogen containing heterocyclic groups, sulphur-containing heterocyclic groups, fluorinated-, chlorinated-, brominated-, iodinated alkanes or aromatic groups, nitroaromatic groups, ethers such as methyl ethers, ethyl ethers, propyl ethers, butyl ethers, pentyl ethers, hexyl ethers and other linear and branched hydrocarbons that contain ether groups.

In a further embodiment, said interacting group (F) contains as part of its structure groups capable of forming hydrogen bonds. Said interacting group (F) may contain as part of its structure groups capable of forming hydrogen bonds such as hydroxyl, amine, carboxylic acid, ester, or ether groups; basic groups such as amines; organic acidic groups such as carboxylic acids, sulfonic acids, boronic acids or phosphonic acids. The chemiresistive material may also contain groups capable of forming hydrogen bonds.

The net negatively charged component (N) comprises at least one organic anionic group. Preferably such an anionic group (N) is a negatively charged anion such as a carboxylate, sulfonate, phosphonate, phenolate or boronate groups. The charged molecule may also contain one or more positively charged groups so long as the net charge is negative.

As will be appreciated, for analyte molecules containing organic acid or organic amine groups, or combination of organic acids and amine groups, the overall charge of the analyte molecule may be adjusted by adjusting the pH of the electrolyte solution.

In a further embodiment, the charged analyte molecule may be generated from a charged molecule or neutral molecule by a chemical process. The chemical process can include but is not limited to electrochemical oxidation/reduction, chemical oxidation/reduction, hydrolysis, ozonolysis, carbonation, hydrogenolysis, elimination, degradation, substitution, addition. The starting molecule may include but is not limited to primary alcohols, aldehydes, alkenes, alkyl benzenes, nitriles, amides, nitrocompounds, aldehydes, ketones. The chemical process may take place in-situ or ex-situ. In the context of the present invention, in-situ as defined as being located in the place of operation, that is, the chemical process occurs inside the device. Ex-situ is defined as being located outside the place of operation, that is, the chemical process occurs separately from the device as a sample preparation step.

In a preferred embodiment, chemical oxidation generates a positively charged analyte molecule from a neutral, positively or negatively charged molecule. The oxidation may take place in-situ or ex-situ.

In another preferred embodiment, chemical oxidation generates a negatively charged analyte molecule from a neutral, positively or negatively charged molecule. The oxidation may take place in-situ or ex-situ.

It is further preferred that the oxidation takes place ex-situ.

In a preferred embodiment, chemical reduction generates a negatively charged analyte molecule from a neutral, positively or negatively charged molecule. The reduction may take place in-situ or ex-situ.

In another preferred embodiment, chemical reduction generates a positively charged analyte molecule from a neutral, positively or negatively charged molecule. The reduction may take place in-situ or ex-situ.

It is further preferred that the reduction takes place ex-situ.

For the generation of a positively charged analyte molecule, it is preferred that the starting molecule is neutral or negatively charged.

For the generation of a negatively charged analyte molecule, it is preferred that the starting molecule is neutral or positively charged.

In yet another embodiment, a neutral molecule is generated from a charged molecule by a chemical process. The chemical process can include but is not limited to electrochemical oxidation/reduction, chemical oxidation/reduction, hydrolysis, ozonolysis, carbonation, hydrogenolysis, elimination, degradation, substitution, addition. Such embodiments may reduce the response of a particular molecule where there is no desire to measure its response in the presence of another charged analyte molecule of interest.

The electrolyte solution may be aqueous or non-aqueous and can include but is not limited to water, urine, blood, sweat, breath, saliva, sputum, tear fluid, spinal fluid, milk, juice, wine, beverages, fermentation broth, seawater, wastewater, freshwater, brackish water, groundwater, ethanol, methanol, dimethylformamide, acetonitrile.

It is preferred that the electrolyte solution be aqueous and can include but is not limited to water, urine, blood, sweat, breath, saliva, sputum, tear fluid, spinal fluid, milk, juice, wine, beverages, fermentation broth, seawater, wastewater, freshwater, brackish water, groundwater.

Other preferred charged analyte molecules include amino acids and peptides, DNA or RNA fragments, charged pharmacologically active drugs, opioids and their derivatives and analogues, charged non-steroidal anti-inflammatory drugs, salicylic acid, charged pesticides, charged herbicides, charged pesticides, charged environmental pollutants, charged metabolites.

In any of the above aspects, or embodiments thereof, the chemiresistive material may comprise a conductive particulate material with connections therebetween comprising of a non-conductive material. The conductive material may be embedded within the non-conductive particulate material. Optionally, the non-conductive particulate material may coat the conductive particulate material in order to render the chemiresistive material able to undergo resistive changes. The non-conductive material may attach to the conductive material via a chemical or physical means. The conductive material may comprise a metallic conductor, an inorganic conductor, an organic conductor, or an organic conducting polymer or mixtures thereof. The non-conductive material may be an organic molecule or a polymer.

In one embodiment, the chemiresistive material comprises a conductive particulate material such as nanoparticles coated with a non-conductive organic material. As used herein, the term "nanoparticle" refers to a material that has at least one length scale that is 1 micron or less. Preferably the nanoparticles have an average diameter of 1 micron or less and is larger than 1 nm in average diameter. Preferred are particles with diameters less than 100 nm and greater than 2 nm. More preferred are particles with diameters less than 50 nm and greater than 2 nm.

The particles that make up the chemiresistor material may adopt a number of shapes, including but not limited to spheres, rods, disks, cubes, plates or they may have an irregular shape or a fractal shape, e.g. multi-pod, star-like or spiky. Preferred are particles that are approximately spherical.

A wide variety of electrically conductive materials may be used for nanoparticles. Preferably the nanoparticles are metals and metal alloys selected from the group consisting of Au, Ag, Ni, Co, Pt, Pd, Cu, Au/Ag, Au/Cu, Au/Ag/Cu, Au/Pt, Au/Pd, Au/Ag/Cu/Pd, Pt/Rh, Ni/Co, and Pt/Ni/Fe. Preferred are nanoparticles consisting of gold, silver, platinum, or palladium either by themselves or as alloys. More preferred are nanoparticles consisting of gold.

In a preferred embodiment the metallic nanoparticles are capped, protected, or coated with a non-conductive material that is an organic ligand.

The term "ligand" as used in the present invention denotes a molecule with one of more binding groups capable of physically or chemically binding to the nanoparticle, and with one or more additional functional groups capable of physically or chemically binding to an analyte molecule.

Ligand binding groups suitable for binding to nanoparticles may include one or more thiol groups, disulfide groups, sulphide groups, phosphine groups, or amine groups.

Functional groups capable of chemically or physically binding to the analyte molecule will depend on the type of analyte that is to be detected and may include but is not limited to hydrocarbon groups such as cyclic or acyclic alkanes, aromatic groups (either single or polyaromatic groups); groups capable of forming hydrogen bonds such as hydroxyl, amine, carboxylic acid, ester, or ether groups; basic groups such as amines; acidic groups such as carboxylic acids, sulfonic acids, phosphonic acids; positively charged groups such as ammonium or pyridinium groups; negatively charged groups such as salts of acids such as carboxylate, sulfonate or phosphonate groups; boronic acid groups that interact with carbohydrates; amino acid or peptide groups; DNA or RNA fragments; crown ethers or their derivatives.

Preferred ligands may include but are not limited to alkane thiols such as ethane thiol, propane thiol, butane thiol, pentane thiol, hexane thiol, heptane thiol, octane thiol, nonane thiol, decane thiol, undecane thiol, dodecane thiol, tridecane thiol, tetradecane thiol, pentadecane thiol, heaxadecane thiol, heptadecane thiol, octadecane thiol, phytanyl thiol, thiophenol, benzyl mercaptan, p-thiocresol, 2-methylbenzenethiol, 3-methylbenzenethiol, mercaptopyridine, mercaptobenzoic acid, mercaptophenylboronic acid, hydroxythiophenol, aminothiophenol, methoxythiophenol, alpha-omega hydroxy alkane thiols, alpha-omega amino alkane thiols, alpha-omega carboxyl alkane thiols, thiol substituted oligoethylene glycols including the monothiol of ethylene glycol, triethylene glycol, tetraethylene glycol, pentaethylene glycol, or hexaethylene glycol, alkane dithiols such as 1,2-ethanedithiol, 1,3-propanedithiol, 1,4-butanedithiol, 1,5-pentanedithiol, 1,6-hexanedithiol, 1,7-hepatnedithiol, 1,8-octanedithiol, 1,9-nonanedithiol, 1,10-decanedithiol, 1,11-undecanedithiol, 1,12-dodecanedithiol, 1,3-tridecanedithiol, 1,14-tetradecanedithiol, 1,5-pentadecanedithiol, 1,16-hexadecanedithiol, 1,17-heptadecanedithiol, 1,18-octadecanedithiol, cysteine.

In one embodiment, mixtures of ligands with different functional groups are used within the same chemiresistor nanoparticle material in order to tailor the chemiresistors interactions with the analyte, thus enabling the formation of different chemiresistors with different selectivities and sensitivities towards various analytes.

As will be appreciated, the symmetrical or mixed disulfides of the above compounds may be readily produced from oxidation of the appropriate thiol and may also be used.

In another embodiment, the chemiresistive material is an organic conductor with an insulating organic molecule or polymer. The conductive organic component is selected from carbon black, graphite, graphene, fullerenes, carbon nanotubes. The term "graphene" as used herein comprises graphite with layers of 5 or less. It is preferred that the graphene is single-layer or double-layer.

The term "carbon nanotubes" as used in the present invention comprises rolled up sheets of graphene. Carbon nanotubes can be single-walled or multi-walled. It is preferred that the carbon nanotubes are single-walled. It is preferred that carbon black comprises particles with an average diameter in the range of 10 nm and 200 nm.

The conductive organic component is typically blended with an insulating polymer.

The insulating polymers are selected from the group containing main-chain carbon polymers, main-chain acyclic heteroatom polymers, main-chain heterocyclic polymers.

Examples include but are not limited to poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(aryines), poly(oxides), poly(carbonates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), poly(diabenzofuirans), poly(phthalides), poly(acetals), poly(anhydrides), carbohydrates.

Nonconductive organic polymer materials; blends and copolymers; plasticized polymers; and other variations including those using the polymers listed here, may also be used.

The insulating component can also be an organic molecule that is functionalised with the organic conductor. Functionalisations include covalent, non-covalent, van der Waals, hydrogen-bonding, pi-pi interactions.

In another embodiment, the chemiresistive material is an organic conductive polymer.

It is preferred that the conductive polymer is poly(aniline), poly(thiophene), poly(pyrrole), poly(acetylene). It is further preferred that the chemiresistive material is an organic conductive polymer/insulator.

In another embodiment, the chemiresistive material is an organic conductor without a non-conducting blend. The conductive material is selected from carbon black, graphite, graphene, C60, carbon nanotubes, preferably carbon nanotubes and graphene.

The chemiresistive material may be prepared by a number of methods such as spray painting, screen printing, solution deposition, layer-by layer depositions, stamping, painting, spin coating, drop deposition, evaporative self-assembly, doctor blading or printing. In particular, various methods of printing exist that are particularly suitable for producing chemiresistive thin films based on solutions of nanoparticles and solutions of ligands. Such printing methods include inkjet printing using thermal printing or piezoelectric printing methods, as well as gravure, and off-set printing.

A particularly preferred method of producing chemiresistors is the use of inkjet printing, either thermal (bubblejet) printing or piezoelectric printing techniques.

In a further preferred embodiment of the present invention, a solution of the nanoparticles is printed, said nanoparticles are stabilized with a capping agent that is readily displaced by one or more ligand groups. The nanoparticle film is subsequently exposed to one or more ligand groups, either sequentially or as a mixture, in order to form the chemiresistor. It is further preferred that the capping agent is N, N'-dimethylamino pyridine (DMAP). It is further preferred that a solution of the nanoparticles is printed, said nanoparticles are stabilized with a capping agent that is readily displaced by one or more ligand groups and that said ligand groups are also deposited onto the printed nanoparticles by inkjet printing, wherein the nanoparticle film is functionalised by the ligands in-situ on the substrate.

It is further preferred that a solution of the nanoparticles is printed by inkjet or micropipette droplet printing, the nanoparticles being gold nanoparticles of between 4 to 8 nm in diameter, with DMAP as the capping agent, formulated as an ink in water at a concentration of between 0.1 to 10% weight/volume, said aqueous solution containing N-methyl-2-pyrrolidone (NMP) at between 0 to 10% weight/volume concentration. The nanoparticle film is subsequently exposed to one or more ligand groups, either sequentially or as a mixture, in order to form the chemiresistor.

It is particularly preferred that a solution of the nanoparticles is printed by inkjet or micropipette droplet printing, the nanoparticles being gold nanoparticles of between 4 to 8 nm in diameter, with DMAP as the capping agent, formulated as an ink in water at a concentration of 1% weight/volume, said aqueous solution containing N-methyl-2-pyrrolidone (NMP) at 4% weight/volume concentration. The nanoparticle film is subsequently exposed to one or more ligand groups, either sequentially or as a mixture, in order to form the chemiresistor.

The chemiresistive material is deposited between electrically conductive electrodes. It is preferred that the electrically conductive electrodes are made from two or more parallel band or circular electrodes. In the case where the electrodes are made from 1 or more sets of band electrodes it is preferred that the distance between adjacent bands is between 10 nm and 10 microns in width and that the width of the electrically conductive electrode pads is between 10 nm and 10 microns.

More preferably in the case where the electrodes are made from 1 or more sets of band electrodes it is preferred that the distance between adjacent bands is between 100 nm and 5 microns in width and that the width of the electrically conductive electrode pads is between 100 nm and 5 microns.

Most preferably in the case where the electrodes are made from 1 or more sets of band electrodes it is preferred that the distance between adjacent bands is between 100 nm and 1 micron in width and that the width of the electrically conductive electrode pads is between 100 nm and 1 micron.

In a further embodiment it is preferred that the electrodes are made from two or more circular band electrodes where the distance between adjacent bands is between 1 to 10 microns in width and that the width of the electrically conductive electrodes is between 1 and 10 microns.

The conductive electrode pads may be fabricated by standard photolithographic means, or by electron beam, focussed ion beam or other suitable methods known to those skilled in the art.

BRIEF DESCRIPTION OF DRAWINGS

Embodiments are described in further detail below, by way of example and with reference to the accompanying drawings, in which:

FIG. 3a) is illustrative in the absence of a gate voltage whilst FIGS. 3b) and 3c) are illustrative in the presence of a negative gate voltage.

FIG. 4a) illustrates a Cationic surfactant, cetyl pyridinium bromide (10 mM), FIG. 4b) illustrates an anionic surfactant, sodium dodecyl sulphate (10 mM), FIG. 4c) illustrates a salt solution, potassium chloride (100 mM) and FIG. 4d) a zwitterionic surfactant, 3-[(3-cholamidopropyl) dimethylammonio]-1-propanesulfonate (100 mM).

DESCRIPTION OF EMBODIMENTS

Figure 1:
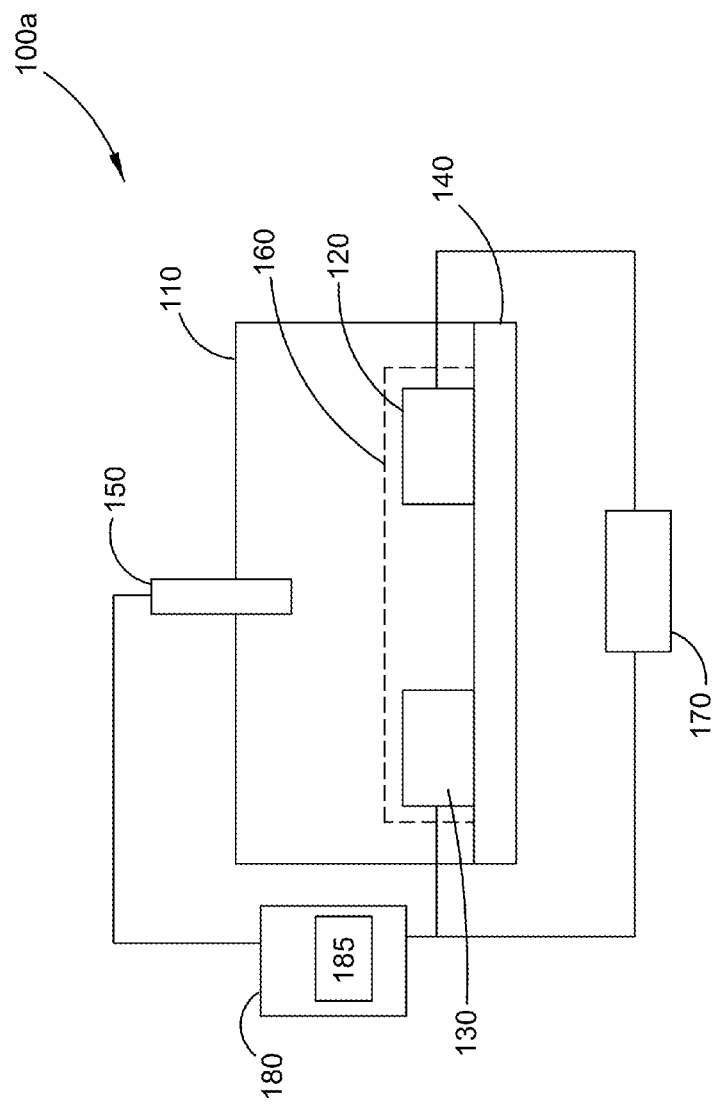
FIG. 1 illustrates a schematic sensor in accordance with one embodiment of the invention.

Referring to FIG. 1, a first embodiment of a sensor 100a is schematically shown. The sensor 100a is provided for measuring the presence or amount of an ionic analyte in an electrolyte solution. The sensor 100a includes two electrically conducting electrodes (120, 130) on an electrically insulating substrate 140, and separated by a distance L, where L is between 10 nm and 100 µm. The sensor 100a further includes a gate formed from an electrically conductive material and a chemiresistor film 160 wherein the impedance of the chemiresistor film 160 changes in the presence of an ionic analyte; and wherein the chemiresistor film is in contact with the electrodes (120, 130). The sensor 100a further includes a potentiostat 180 configured to apply an electrical potential difference between the gate electrode and the chemiresistor film. The sensor 100a further includes a controller 185 to selectively control the potential generator means 180 to apply either a positive electric potential or a negative electric potential to the gate electrode 150 relative to the potential of the chemiresistor film 160.

The sensor 100a further includes means 170 adapted to apply a voltage signal between said pair of electrically conducting electrodes 120, 130 to enable measurement of the resistance of the chemiresistor film 160. Associated with means 170 is a device for measuring the resistance of said chemiresistor film 160 under the applied voltage signal.

It will be appreciated that when applying a potential difference between two electrodes in an electrolyte solution that charges will accumulate at the materials surface.

The present inventors have found that application of a potential difference between a gate electrode 150 and the chemiresistive film 160, increases the concentration of charged analyte molecules in the vicinity of the chemiresistive film 160, and allows the charged molecules to penetrate into the chemiresistive film 160. Without wishing to be bound by any scientific theory, the inventors presently believe that the gate potential facilitates penetration of charged molecules into the chemiresistive film 160; that is into a material that would normally be poorly penetrated by charged molecules. Penetration of the charged molecules into the chemiresistive film 160 causes swelling of the film 160 as the distance between the conductive regions increases. The subsequent swelling decreases the current, which therefore increases the resistance of the chemiresistive film 160.

Furthermore, the present inventors have now found that chemiresistive films/materials that interact with particular functionalities (that is, said interaction groups (F)) on the charged analyte molecules provide even further enhanced sensor response during application of a gate potential.

Figure 2:
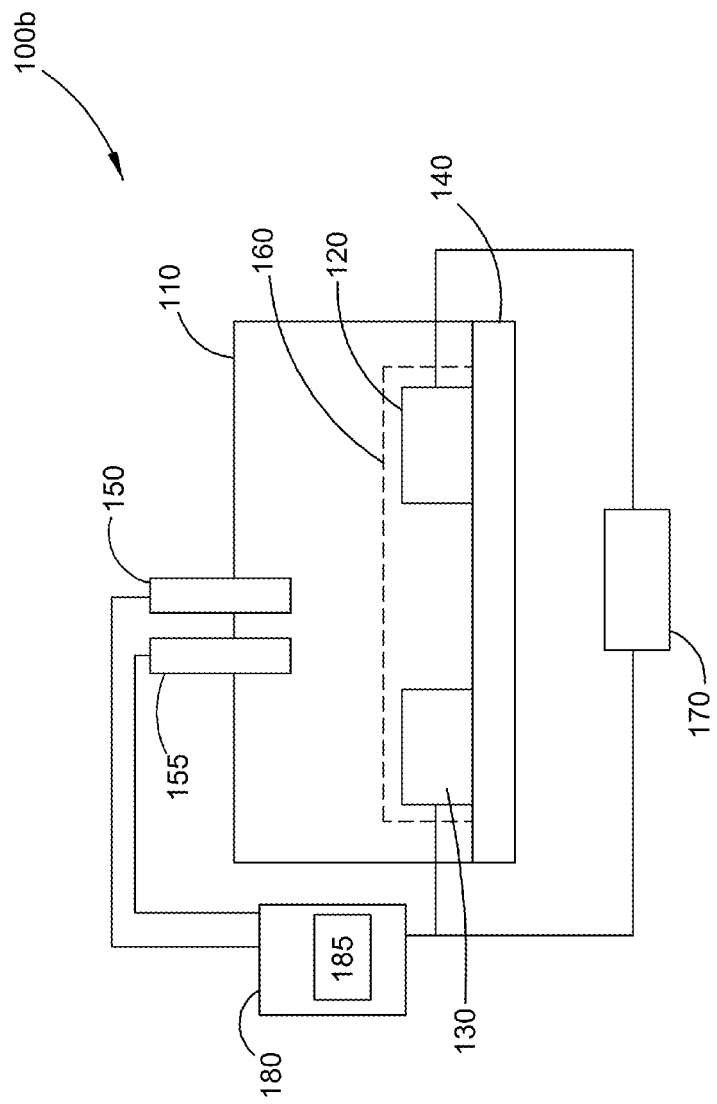
FIG. 2 illustrates a schematic sensor in accordance with a further embodiment of the invention.

Referring to FIG. 2, a second embodiment of a sensor 100b is schematically illustrated. Sensor 100b provided for measuring the presence or amount of an ionic analyte in an electrolyte solution. Like numbers refer to like elements throughout.

The sensor 100b includes two electrically conducting electrodes (120, 130) on an electrically insulating substrate 140, and separated by a distance L, where L is between 10 nm and 100 µm. The sensor 100b further includes a gate electrode comprising a counter electrode 150 and a reference electrode 155 combination, and a chemiresistor film 160, wherein the impedance of the chemiresistor film 160 changes in the presence of an ionic analyte; and wherein the chemiresistor film is in contact with the electrodes (120, 130). The sensor 100b further includes a potentiostat 180 configured to apply an electrical potential difference between the gate electrode and the chemiresistor film. The sensor 100b further includes a controller 185 to selectively control the potential generator means 180 to apply either a positive electric potential or a negative electric potential to the gate electrode relative to the potential of the chemiresistor film 160.

In order that the nature of the present invention be more clearly understood preferred forms thereof will now be described with reference to the following non-limiting examples.

The inventors have proven that it is possible to externally modulate the electrical resistance of a gold nanoparticle film by placing an external gate electrode in an aqueous solution containing species that are both (i) charged and (ii) organic. Gold nanoparticle films do not intrinsically exhibit transistor-like properties and as such no variation of the source-drain current has been previously observed upon applying a gate voltage across a gate dielectric.

Figure 3:
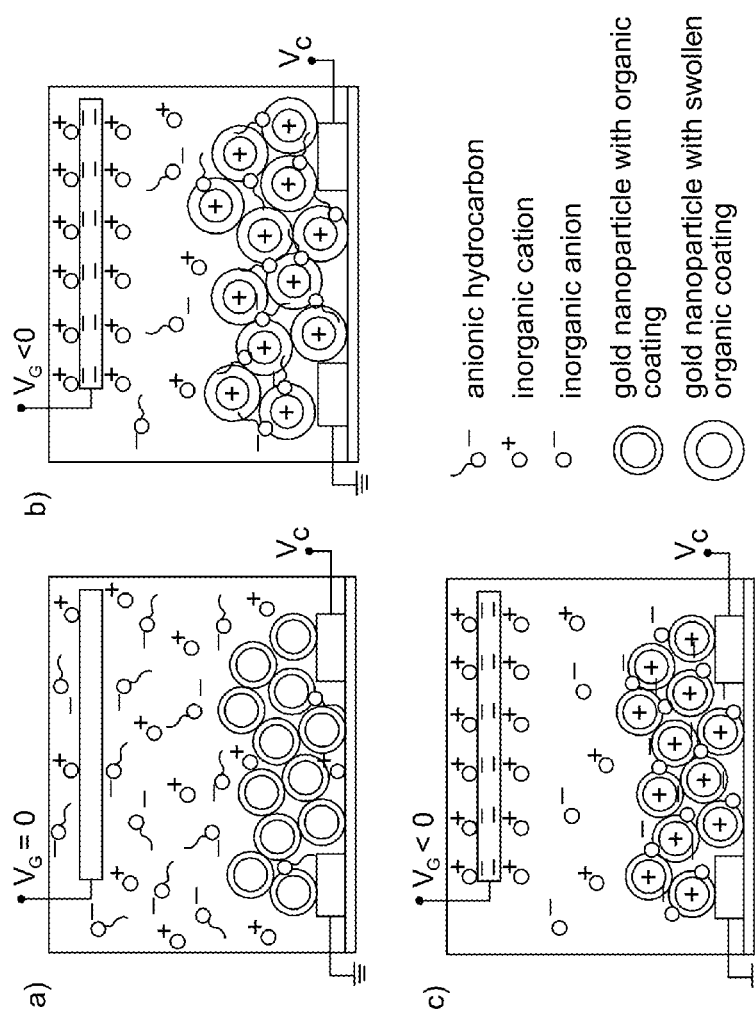
FIG. 3 illustrates a schematic diagram of a gold nanoparticle film in the presence of a charged species.

FIG. 3 shows a schematic diagram of a gold nanoparticle film in the presence of a charged species. FIG. 3a) is illustrative in the absence of a gate voltage ($V_G$=0). As shown, anionic hydrocarbons and inorganic cations present in solution interact minimally with the gold nanoparticle film and do not significantly alter the electrical resistance across the film (applied voltage, $V_C$). FIG. 3b) is illustrative in the presence of a negative gate voltage ($V_G$<0). In this example, the anionic hydrocarbons preconcentrate into the gold nanoparticle film, swell the organic coating of the gold nanoparticles, and increase the electrical resistance across the film. FIG. 3c) again illustrative of a negative gate voltage, inorganic anions are driven to the film but do not significantly alter the electrical resistance across the film.

The electronic conduction a of gold nanoparticle films is based on an electron tunneling mechanism $\sigma \propto \exp[-\beta L]\exp$

[$-E_c/kT$]; where $\beta$ is the electron tunneling decay constant, L is the interparticle separation, $E_c$ is the Coulomb blockade energy and k is the Boltzmann constant. Thus changes in any of the variables could result in electrical resistance modulation of the nanoparticle film.

Figure 4:
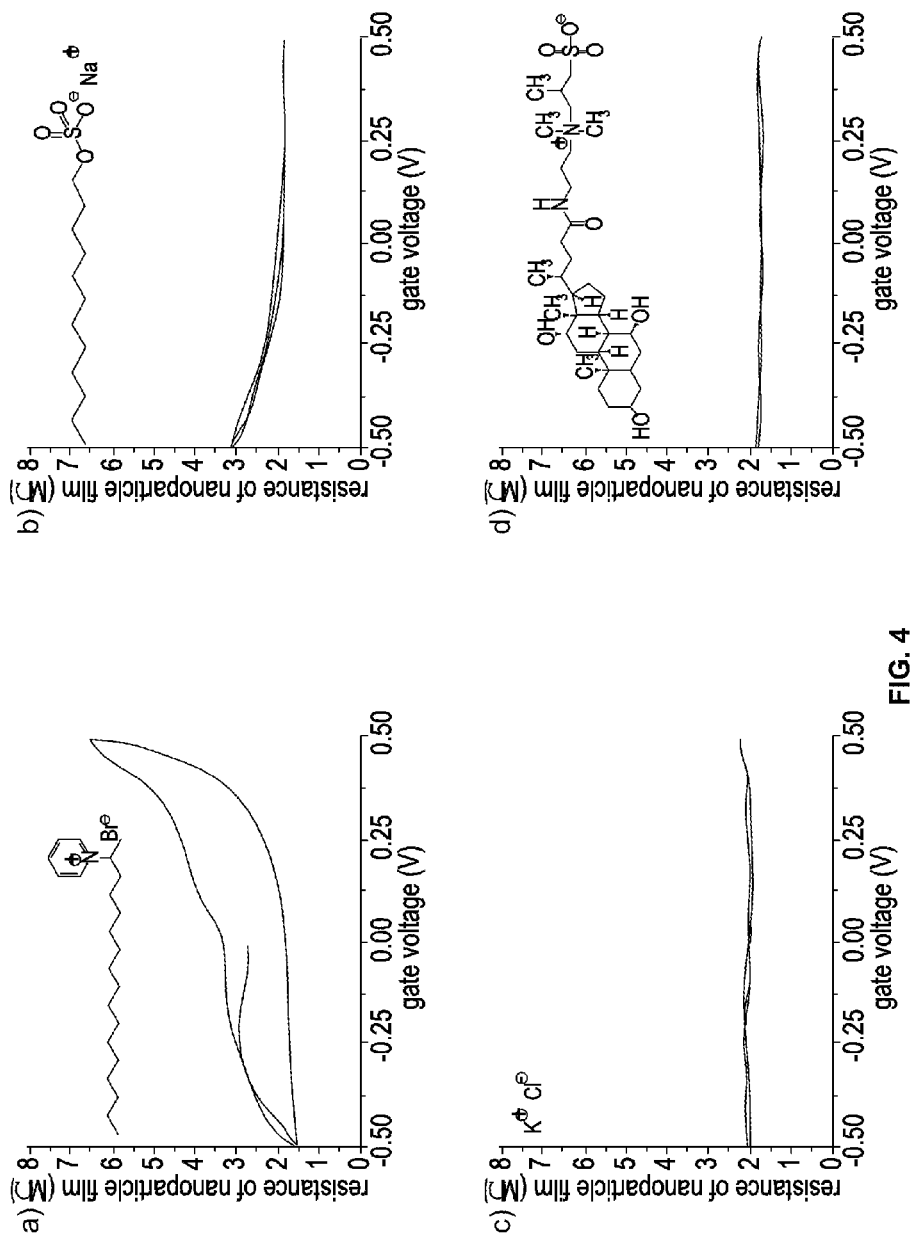
FIG. 4 illustrates modulation of the electrical resistance of a 1-hexanethiol-coated gold nanoparticle film by sweeping the gate voltage at 10 mV/s in the presence of a charged species.

To effectively modulate the nanoparticle film resistance with an external gate electrode the inventors have determined that the charge of the chemical species plays an important role. When the organic chemical species is positively charged, e.g. cetyl pyridinium bromide (10 mM), a 1-hexanethiol-coated gold nanoparticle film is readily modulated upon applying a positive gate voltage, as signified by an increase in resistance (FIG. 4a). The positive gate voltage induces negative charges inside the nanoparticles which drives the positively charged ions (cetyl pyridinium) into the film where the organic component of the species is believed to intercalate with the hexanethiolate coating and thereby increase the interparticle separation. As the nanoparticle films conduct via electron tunneling between the gold cores and along the alkanethiolate coating, this subsequently increases the resistance. If the organic chemical species is negatively charged, e.g. sodium dodecyl sulphate (10 mM), then the resistance modulation occurs at negative gate voltages as the nanoparticle film is now positively charged (FIG. 4b). The small inorganic counter ions in the two illustrated examples do not play a significant role in the resistance modulation and this was further confirmed by a solution containing potassium chloride ions (FIG. 4c) at ten times the ionic strength of the previous examples. Furthermore, if the electrolyte solution contains zwitterionic molecules, e.g. 3-[(3-cholamidopropyl)dimethylammonio]-1-propanesulfonate, then the resistance of the nanoparticle film can also not be modulated by the gate (FIG. 4d). These results are of significance because it allows selective modulation of the gold nanoparticle film by species that are net positively or negatively charged through the polarity of the gate electrode.

It is also of importance for the modulation effects to be reversible and the inventors have shown that the speed in which hexanoic acid is removed from the film could be dramatically increased by applying a positive gate voltage during a water flushing step. By applying a gate voltage of +0.5 V, within 120 s there was >90% return to the original baseline resistance. This implies that gold nanoparticle films are electrically switchable in that charged hydrocarbons can alter the electron tunneling pathways by partitioning into and out of the film with different gate polarities.

EXAMPLES

Example 1. Formation of the Chemiresistor

Glass microscope slides were patterned with an array of eight interdigitated gold microelectrodes (10 fingers, each finger 3 mm long, 5 microns wide and separated by 5 microns) using a conventional photolithography technique (Raguse et al., Anal. Chem. 2007, 79, 7333).

The glass slides patterned with the eight interdigitated microelectrodes were pre-treated with a silylating agent (mercaptopropyl triethoxysilane, MPTES) prior to deposition of the chemiresistive material, gold nanoparticles, for better adhesion of the nanoparticles to the glass and the electrode surface. Thus, the glass slides were immersed in a solution containing 2% v/v MPTES in toluene for two hours, followed by rinsing with copious amounts of toluene and drying under a gentle stream of nitrogen. The treated glass slides were then baked in an oven at 110° C. for one hour.

Subsequently, 1.8 nL of an aqueous solution containing 1% w/v DMAP-gold nanoparticles and 4% N-methyl pyrrolidone were inkjet deposited onto the microelectrodes on the glass slide and allowed to dry (Chow et al., Anal. Chim. Acta. 2009, 632, 135). The nanoparticle film was then functionalised with 1 mM 1-hexanethiol in acetonitrile for 2 hours, and then rinsed with acetonitrile to result in the formation of the 1-hexanethiol-functionalised gold nanoparticle film. The nanoparticle film on the microelectrode-patterned glass slide and an external gate electrode were placed in solution to form the chemiresistor.

Example 2. Correlation Between the Gate Voltage and the Net Charge of the Hydrocarbon The device was prepared as in example 1, and was placed in a well plate solution holder such that the gold nanoparticle film bridged by the interdigitated electrodes and the silver/silver chloride gate electrode were in contact with the electrolyte solution (100 microliters of cetyl pyridinium bromide, CPB; sodium dodecyl sulfate, SDS; or 3-[(3-cholamidopropyl)dimethylammonio]-1-propanesulfonate, CHAPS). The current through the gold nanoparticle film was measured by biasing the potential of the interdigitated electrodes at 100 mV while the potential between the gate electrode and one of the interdigitated electrodes was swept between +500 mV and −500 mV from an initial potential of 0 mV using a Multi Autolab with M101 potentiostat and BA bipotentiostat modules (Autolab, The Netherlands) as illustrated in FIG. 1. From Ohm's Law, the resistance of the gold nanoparticle film between the interdigitated electrodes can be obtained. In Table 1, the resistance of the gold nanoparticle film increases with positive gate voltages in the presence of 10 mM CPB.

TABLE 1

Resistance of the gold nanoparticle film with varying gate voltages in the presence of 10 mM CPB (sweep rate 10 mV/s).

| Sweep Direction | Gate voltage (mV) | Resistance of gold nanoparticle film (ohms) |
|---|---|---|
| Forward | −500 | 1515634 |
|  | −400 | 1626203 |
|  | −300 | 1711123 |
|  | −200 | 1774120 |
|  | −100 | 1806395 |
|  | 0 | 1839865 |
|  | 100 | 1953965 |
|  | 200 | 2199933 |
|  | 300 | 2636415 |
|  | 400 | 3594165 |
| Backward | 500 | 6536605 |
|  | 400 | 5462244 |
|  | 300 | 4570791 |
|  | 200 | 4199410 |
|  | 100 | 3808461 |
|  | 0 | 3388274 |
|  | −100 | 3262120 |
|  | −200 | 3152891 |
|  | −300 | 2834847 |
|  | −400 | 2454716 |
|  | −500 | 1614187 |

Table 2 shows the resistance observed for an anionic hydrocarbon (SDS). The portion of the gate potential sweep from −500 mV to +500 mV is shown. At negative gate voltages, an increase in resistance is observed.

TABLE 2

Resistance of the gold nanoparticle film with varying gate voltages in the presence of 10 mM SDS (sweep rate 10 mV/s).

| Gate voltage (mV) | Resistance of gold nanoparticle film (ohms) |
| --- | --- |
| −500 | 3128210 |
| −400 | 2845185 |
| −300 | 2472683 |
| −200 | 2256283 |
| −100 | 2146188 |
| 0 | 2031494 |
| 100 | 1926396 |
| 200 | 1869253 |
| 300 | 1830615 |
| 400 | 1893010 |
| 500 | 1897394 |

The resistance of the gold nanoparticle film in the presence of a zwitterionic molecule (CHAPS) is shown in Table 3. As the net charge of a zwitterionic molecule is zero, the application of a negative or positive gate voltage does not significantly alter the resistance of the nanoparticle film.

TABLE 3

Resistance of the gold nanoparticle film with varying gate voltages in the presence of 100 mM CHAPS (sweep rate 10 mV/s).

| Gate voltage (mV) | Resistance of gold nanoparticle film (ohms) |
| --- | --- |
| −500 | 1780870 |
| −400 | 1784749 |
| −300 | 1769330 |
| −200 | 1745765 |
| −100 | 1694312 |
| 0 | 1689943 |
| 100 | 1684730 |
| 200 | 1690815 |
| 300 | 1706667 |
| 400 | 1717400 |
| 500 | 1748559 |

In the presence of 100 mM KCl, as shown in Table 4, the variation in the resistance between gate voltages of −500 mV and +500 mV is less than 5%.

TABLE 4

Resistance of the gold nanoparticle film with varying gate voltages in the presence of 100 mM KCl (sweep rate 10 mV/s).

| Gate voltage (mV) | Resistance of gold, nanoparticle film (ohms) |
| --- | --- |
| −500 | 2096481 |
| −400 | 2075237 |
| −300 | 2085805 |
| −200 | 2059585 |
| −100 | 2005386 |
| 0 | 1985939 |
| 100 | 1990765 |
| 200 | 2005386 |
| 300 | 2045443 |
| 400 | 2091130 |
| 500 | 2232457 |

Example 3. Repeated Potential Switching of Chemiresistor

The device was prepared as in examples 1 and 2, and was exposed to a solution containing SDS. To demonstrate that the chemiresistor resistance upon exposure to a charged hydrocarbon is reversible, the gate voltage was switched between +500 mV and −500 mV, 10 times at interval of 2 min. Table 5 illustrates the resistance of the gold nanoparticle film in a solution containing 1 mM SDS upon repeated gate potential pulses of −500 mV and +500 mV (sampled at the end of each pulse). The application of −500 mV increases the resistance of the film, whereas the application of +500 mV decreases the resistance of the film.

TABLE 5

Resistance of the gold nanoparticle film in 1 mM SDS upon applying gate potential pulses of −500 mV and +500 mV.

| Cycle number | Resistance with +500 mV gate voltage (ohms) | Resistance with −500 mV gate voltage (ohms) |
| --- | --- | --- |
| 1 | $1.34 \times 10^6$ | $4.23 \times 10^6$ |
| 2 | $1.39 \times 10^6$ | $4.26 \times 10^6$ |
| 3 | $1.42 \times 10^6$ | $4.29 \times 10^6$ |
| 4 | $1.45 \times 10^6$ | $4.30 \times 10^6$ |
| 5 | $1.47 \times 10^6$ | $4.30 \times 10^6$ |
| 6 | $1.49 \times 10^6$ | $4.29 \times 10^6$ |
| 7 | $1.50 \times 10^6$ | $4.31 \times 10^6$ |
| 8 | $1.52 \times 10^6$ | $4.32 \times 10^6$ |
| 9 | $1.54 \times 10^6$ | $4.34 \times 10^6$ |
| 10 | $1.55 \times 10^6$ | $4.34 \times 10^6$ |

Example 4. Correlation of the Resistance Change with the Chain Length of the Charged Analyte The device was prepared as in example 1, and was placed in a flow cell with a moulded silicone gasket to form the flow channel (50 mm long, 2.9 mm wide and 1.6 mm high) and a top perspex plate with inlet and outlet ports. The array of eight gold nanoparticle films bridged by the interdigitated electrodes and a gold wire gate electrode were all exposed to two different solutions (water and water with the charged analyte) in this flow cell configuration. The gold wire was inserted into the flow cell by piercing the wire through both ends of the silicone gasket. The solution was delivered to the flow channel via two fluid reservoirs which held the water and charged analyte solution, respectively, using a peristaltic pump. The charged analyte consisted of alkanoic acids of different carbon chain lengths (acetic acid, propanoic acid, butanoic acid, pentanoic acid, hexanoic acid, heptanoic acid, octanoic acid, nonanoic acid and decanoic acid). The resistance of the gold nanoparticle film was measured by biasing the potential between the interdigitated electrodes at 100 mV using an 8-channel electrical measurement system built in-house with a 16-channel e-corder unit from eDAQ, while the potential between the gate and one of the interdigitated electrodes was held constant (0 mV or −500 mV) for 6 min using an eDAQ potentiostat (FIG. 1). In a typical experiment, the baseline resistance of the nanoparticle film was determined in a flow solution of water for 2 min, then in a flow solution of the charged analyte solution for 3 min, and then in water for 1 min. From the initial resistance of the gold nanoparticle film in water and the final resistance of the gold nanoparticle film in the charged analyte solution, the relative change in resistance due to exposure of the charged analyte solution can be determined.

Tables 6 and 7 show that there is an increase in the relative resistance change with increasing carbon chain length. The increase can be correlated to the increasing distribution coefficient of the molecule for the nanoparticle film with increasing hydrophobicity.

TABLE 6

Relative resistance change of the gold nanoparticle film in the presence of different alkanoic acids (50 mM) in water with 0 mV or −500 mV gate voltage.

| Alkanoic acid | Relative resistance change (%) with gate voltage of 0 mV | Relative resistance change (%) with gate voltage of −500 mV |
|---|---|---|
| Acetic acid | 1.2 ± 0.3 | 8.3 ± 1.7 |
| Propanoic acid | 6.9 ± 1.0 | 25.4 ± 2.5 |
| Butanoic acid | 36.9 ± 7.8 | 67.8 ± 10.1 |
| Pentanoic acid | 208 ± 45 | 453 ± 163 |
| Hexanoic acid | 719 ± 265 | 1030 ± 490 |

TABLE 7

Relative resistance change of the gold nanoparticle film in the presence of different alkanoic acids (0.05 mM) in water with 0 mV or −500 mV gate voltage.

| Alkanoic acid | Relative resistance change (%) with gate voltage of 0 mV | Relative resistance change (%) with gate voltage of −500 mV |
|---|---|---|
| Hexanoic acid | 2.6 ± 0.6 | 30.8 ± 6.1 |
| Heptanoic acid | 12.8 ± 3.6 | 82.2 ± 34.4 |
| Octanoic acid | 15.7 ± 5.0 | 126.3 ± 37.9 |
| Nonanoic acid | 16.6 ± 3.6 | 236.5 ± 60.5 |
| Decanoic acid | 26.3 ± 3.8 | 314.5 ± 67.6 |

Example 5. Regeneration of the Chemiresistor

The device was prepared as in examples 1 and 4, and the gate voltage was held at a constant potential for the entire water/charged analyte in water solution/water duration. In order to completely remove the charged analyte during the water flushing, the polarity of the gate-source voltage was made opposite to that of the analyte charge. Following exposure to 0.5 mM hexanoic acid, where the potential was held at −500 mV, a gate potential of +500 mV was applied under a constant flow of water for 2 min. Table 8 shows the resistance of the gold nanoparticle film (+100 mV applied across the interdigitated electrodes) at the end of each stage of the exposure/gate voltage period. By keeping the gate potential at −500 mV during flushing with water (for 1 min), there is a 36% recovery to the original baseline, whereas by switching the gate potential to +500 mV for a further 2 min following the 1 min flushing, the recovery to the original baseline is increased to 90%.

TABLE 8

Resistance of the gold nanoparticle upon the application of different conditions.

| Gate potential (mV) | Solution | Resistance of gold nanoparticle film (ohms) |
|---|---|---|
| −500 | Water | 927603 |
| −500 | Hexanoic acid in water | 1534404 |
| −500 | Water | 1313629 |
| +500 | Water | 988112 |

Example 6. Determination of Hexanoic Acid in the Absence and Presence of a Gate Voltage The device was prepared as in examples 1 and 5, and exposed to a range of hexanoic acid concentrations at 0 and −500 mV gate voltage. Table 9 shows the relative resistance change in response to hexanoic acid. At a gate voltage of −500 mV compared to at 0 mV, there is an enhancement in the relative resistance change. The enhancement factor varies with the concentration of hexanoic acid, as it is known that when a weak acid is added to water, it will partially dissociate, and the extent of dissociation depends on the concentration of the acid.

TABLE 9

Relative resistance change of the gold nanoparticle film in the presence of hexanoic acid in water with 0 mV and −500 mV gate voltage.

| Total concentration of hexanoic acid (M) | Relative resistance change (%) with gate voltage of 0 mV | Relative resistance change (%) with gate voltage of −500 mV |
|---|---|---|
| 5E−9 | 0 | 0.15 ± 0.07 |
| 1E−8 | 0 | 0.21 ± 0.11 |
| 2E−8 | 0 | 0.24 ± 0.06 |
| 5E−8 | 0 | 0.31 ± 0.07 |
| 1E−7 | 0 | 0.37 ± 0.12 |
| 2E−7 | 0 | 0.83 ± 0.29 |
| 5E−7 | 0 | 1.7 ± 0.3 |
| 1E−6 | 0 | 1.7 ± 0.6 |
| 2E−6 | 0.27 ± 0.12 | 2.9 ± 0.4 |
| 5E−6 | 0.35 ± 0.14 | 7.5 ± 1.3 |
| 1E−5 | 0.69 ± 0.17 | 13.7 ± 1.6 |
| 2E−5 | 0.82 ± 0.14 | 16.4 ± 0.7 |
| 5E−5 | 1.9 ± 0.2 | 30.8 ± 6.1 |
| 1E−4 | 2.9 ± 0.2 | 36.4 ± 9.3 |
| 2E−4 | 4.0 ± 1.0 | 39.2 ± 1.7 |
| 5E−4 | 9.4 ± 3.4 | 61.1 ± 8.1 |
| 1E−3 | 13.3 ± 1.5 | 81.2 ± 5.2 |
| 2E−3 | 21.6 ± 3.3 | 91.3 ± 6.4 |
| 5E−3 | 28.7 ± 2.7 | 131 ± 15 |
| 1E−2 | 60.7 ± 2.7 | 303 ± 25 |
| 2E−2 | 107 ± 12 | 381 ± 96 |
| 5E−2 | 719 ± 265 | 1029 ± 489 |

Example 7. Determination of Ibuprofen in the Absence and Presence of a Gate Voltage To demonstrate the utility of gold nanoparticle films as sensors for charged organic molecules, the inventors tested the presence of ibuprofen ((R,S)-α-methyl-4-(2-methylpropyl) benzeneacetic acid), an ionizable organic acid group commonly used as an non-steroidal anti-inflammatory pharmaceutical.

Figure 5:
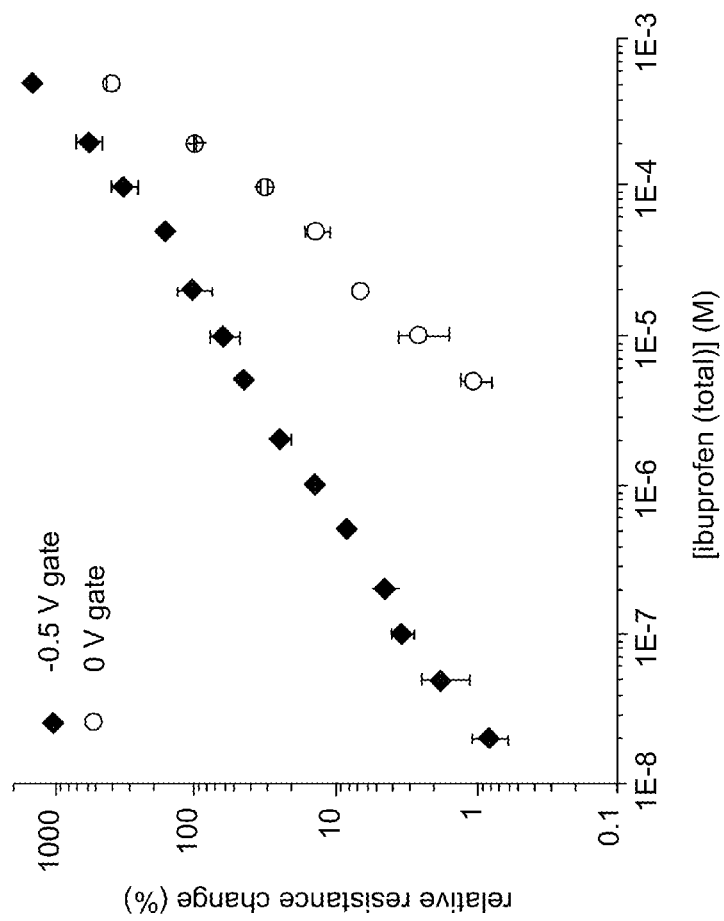
FIG. 5 illustrates the relative resistance changes of a 1-hexanethiol-coated gold nanoparticle film chemiresistor in the presence of ibuprofen with an applied gate voltage of 0 V and −500 mV.

The device was prepared as in example 1 and 5, except that data were acquired and recorded with a Multi Autolab (Autolab, The Netherlands). The chemiresistor was exposed to a range of ibuprofen concentrations at 0 and −500 mV gate voltage. Table 10 and FIG. 5 shows the relative resistance change in response to ibuprofen. At a gate voltage of −500 mV compared to at 0 mV, there is an enhancement in the relative resistance change, a remarkably high resistance change of 1400% with gate control. As the concentration of ibuprofen decreased, so did the fraction of neutral species, which at 0 V gate bias was signified by a rapid decline in the response sensitivity. Conversely, the presence of a gate electrode was able to progressively track nanoparticle resistance changes induced by charged ibuprofen down to a total ibuprofen concentration of 20 nM (99.95% charged form). This represents a 250-fold enhancement in detection limit with gate modulation. The enhancement factor varies with the concentration of ibuprofen acid, as it known that when a weak acid is added to water, it will partially dissociate, and the extent of dissociation depends on the concentration of the acid.

TABLE 10

Relative resistance change of the gold nanoparticle film in the presence of ibuprofen in water with 0 mV and −500 mV gate voltage.

| Total concentration of ibuprofen (M) | Relative resistance change (%) with gate voltage (GV) of 0 mV | Relative resistance change (%) with GV of −500 mV |
|---|---|---|
| 2E−8 | 0 | 0.80 ± 0.22 |
| 5E−8 | 0 | 1.7 ± 0.7 |
| 1E−7 | 0 | 3.3 ± 0.6 |
| 2E−7 | 0 | 4.3 ± 0.6 |
| 5E−7 | 0 | 8.1 ± 0.7 |
| 1E−6 | 0 | 13.7 ± 0.7 |
| 2E−6 | 0 | 24.3 ± 3.5 |
| 5E−6 | 1.0 ± 0.3 | 44.8 ± 3.8 |
| 1E−5 | 2.5 ± 1.0 | 63.5 ± 15.5 |
| 2E−5 | 6.5 ± 0.7 | 103 ± 27 |
| 5E−5 | 14.0 ± 2.9 | 163 ± 14 |
| 1E−4 | 31.8 ± 2.2 | 324 ± 66 |
| 2E−4 | 101 ± 3 | 577 ± 118 |
| 5E−4 | 392 ± 36 | 1427 ± 148 |

Example 8. Determination of Ethyl Octanoate Via the Hydrolysis of Ethyl Octanoate to Octanoic Acid A solution of ethyl octanoate in 100 mL water was prepared and transferred to a round bottom flask. An excess of sodium hydroxide was added to the flask. The solution was then refluxed for 1 hour and the ethanol that was formed was distilled off. The sodium octanoate was then worked up with an excess of dilute hydrochloric acid to form octanoic acid. The octanoic acid was then distilled into a 100 mL volumetric flask and filled to the mark with water. The octanoic acid solution was then tested as described in example 6, substituting hexanoic acid for octanoic acid.

Example 9. Determination of a Mixture of Toluene and Hexanoic Acid

The device was prepared as in example 1 in triplicate (i.e. electrodes 1, 2 and 3 in Tables 13 and 14) and exposed to a mixture of toluene and hexanoic acid in water. Five different mixtures of known concentrations were prepared using a two-level, two-component full-factorial design with a centre point as illustrated in Tables 11 and 12. Each solution was tested as described in example 7 at a gate voltage of 0 and −500 mV. Tables 13 and 14 show the relative resistance (%) change in response to toluene and hexanoic acid. Data analysis, based on the % change towards the analyte solution at 0 V and −500 mV applied gate voltage, was performed using partial least squares regression for quantification of toluene and hexanoic acid. Of the 15 measurements (5 samples, 3 replicates), 12 were used as a training set and 3 were used as a test set. The predicted concentration of each of the samples is shown in Table 15.

TABLE 11

Concentrations of toluene and hexanoic acid used for the two-level, two-component full-factorial design with a centre point.

| Level | Concentration of toluene (mg/L) | Concentration of hexanoic acid (mg/L) |
|---|---|---|
| −1 | 0 | 0 |
| 0 | 10 | 5 |
| 1 | 20 | 10 |

TABLE 12

Levels of toluene and hexanoic acid for the experimental design.

| Run | Level of toluene | Level of hexanoic acid |
|---|---|---|
| 1 | −1 | −1 |
| 2 | −1 | 1 |
| 3 | 0 | 0 |
| 4 | 1 | −1 |
| 5 | 1 | 1 |

TABLE 13

Relative resistance change (%) of the gold nanoparticle film in the presence of toluene and hexanoic acid in water at 0 mV gate voltage.

| Sample | Relative resistance change (%) with GV of 0 mV | | |
|---|---|---|---|
| | Electrode 1 | Electrode 2 | Electrode 3 |
| water | 0.05 | 0 | 0 |
| 10 mg/L hexanoic acid | 5.1 | 4.6 | 3.3 |
| 10 mg/L toluene + 5 mg/L hexanoic acid | 7.5 | 6.9 | 6.3 |
| 20 mg/L toluene | 9 | 8.7 | 8.8 |
| 20 mg/L toluene + 10 mg/L hexanoic acid | 13.6 | 12.6 | 11 |

TABLE 14

Relative resistance change (%) of the gold nanoparticle film in the presence of toluene and hexanoic acid in water at −500 mV gate voltage.

| Run | Relative resistance change (%) with gate voltage of −500 mV | | |
|---|---|---|---|
| | Electrode 1 | Electrode 2 | Electrode 3 |
| water | 0 | 0 | 0 |
| 10 mg/L hexanoic acid | 36.8 | 35.2 | 33.8 |
| 10 mg/L toluene + 5 mg/L hexanoic acid | 24.8 | 23 | 23.4 |
| 20 mg/L toluene | 8.7 | 8.9 | 8.1 |
| 20 mg/L toluene + 10 mg/L hexanoic acid | 45 | 41.9 | 42.6 |

TABLE 15

Predicted and actual concentrations of toluene and hexanoic acid as determined using partial least squares regression using the data obtained and shown in Tables 13 and 14.

| Sample | True concentration of toluene (mg/L) | Predicted concentration of toluene (mg/L) | True concentration of hexanoic acid (mg/L) | Predicted concentration of hexanoic acid (mg/L) |
|---|---|---|---|---|
| 1 | 0.000 | −0.520 | 0.000 | −0.032 |
| 2 | 0.000 | −0.520 | 0.000 | −0.032 |
| 3 | 20.000 | 20.162 | 0.000 | −0.049 |
| 4 | 20.000 | 19.819 | 0.000 | −0.179 |
| 5 | 0.000 | 2.067 | 10.000 | 10.166 |
| 6 | 0.000 | 1.238 | 10.000 | 9.809 |
| 7 | 0.000 | −1.708 | 10.000 | 9.766 |
| 8 | 10.000 | 11.686 | 5.000 | 5.575 |
| 9 | 10.000 | 10.657 | 5.000 | 5.185 |
| 10 | 20.000 | 21.605 | 10.000 | 10.144 |
| 11 | 20.000 | 19.918 | 10.000 | 9.463 |
| 12 | 20.000 | 15.598 | 10.000 | 10.186 |
| 13 | 0.000 | −0.391 | 0.000 | −0.048 |
| 14 | 20.000 | 19.332 | 0.000 | 0.108 |
| 15 | 10.000 | 8.997 | 5.000 | 5.500 |

The analysis shows that quantification of each of the components is possible by using a virtual sensor array with one physical sensor, by performing the measurement at different gate voltages.

As has been shown, the application of a potential to an external gate electrode induces charges at the gold nanoparticle film and facilitates the movement of oppositely charged species to the film. It should be appreciated that the inventors have investigated conduction occurring across the film rather than through the film. Measuring the current through (at) the nanoparticle film is the more conventional approach in three-electrode electrochemistry.

The invention has implications for the development of devices that can be modulated by combinations of both chemical signals and an applied electrical gate potential. Of significance is the ability to detect small charged molecules (<~2000 daltons) using chemiresistors at levels beyond standard sensitivities as well as the possibility of distinguishing molecules that are neutral, positively or negatively charged with a single sensor.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:
1. A sensor for measuring the presence or amount of an ionic analyte in an electrolyte solution, said sensor comprising:
  (i) a pair of electrically conducting electrodes on an electrically insulating substrate, and separated by a distance L, where L is between 10 nm and 100 µm;
  (ii) a chemiresistor film having an impedance Z, wherein Z changes in the presence of an ionic analyte; the chemiresistor film is in contact with the pair of electrodes, and the chemiresistor film comprises a conductive particulate material with junctions therebetween comprising a non-conductive material;
  (iii) a gate electrode formed from an electrically conductive material;
  (iv) a potential generator means connected to the gate electrode and the chemiresistor film, in order to apply an electrical potential difference between the gate electrode and the chemiresistor film;
  (v) a controller connected to the potential generator to selectively control the potential generator means to apply either a positive electric potential or a negative electric potential to the gate electrode relative to a potential of the chemiresistor film; and
  (vi) a voltage power supply connected to each of the pair of electrically conducting electrodes to apply a voltage signal between the pair of electrically conducting electrodes to enable measurement of a resistance of the chemiresistor film,
  wherein the gate electrode is externally positionable in the electrolyte solution.

2. A sensor according to claim 1, wherein the gate electrode is one of a gold electrode, a platinum electrode, a palladium electrode, a silver electrode, a carbon electrode, an Ag/AgCl gate electrode, and an Ag/AgCl gate electrode where the silver has been chlorided.

3. A sensor according to claim 1, wherein the gate electrode comprises a counter electrode and a reference electrode.

4. A sensor according to claim 3, wherein the counter electrode is formed from one of gold, platinum, palladium, silver and a conductive carbon material.

5. A sensor according to claim 3, wherein the reference electrode is selected from one of a Ag/AgCl electrode, a non-aqueous Ag/Ag+ electrode, a mercury/mercurous sulphate electrode and a saturated calomel electrode.

6. A sensor according to claim 1, where the pair of electrically conducting electrodes are each formed from either an inert material selected from gold, palladium, platinum, silver, copper and nickel or a conductive material based on conductive carbon selected from carbon black, graphene and carbon nanotubes.

7. A sensor according to claim 1, wherein the pair of electrically conducting electrodes are respectively coated with a layer of an inert material, the inert material characterised by:
  (a) having a dielectric constant that is less than that of water;
  (b) being at least partially impermeable towards ions; and
  (c) having a thickness less than 2 nanometers.

8. A sensor according to claim 7 wherein each of the pair of electrically conducting electrodes are formed from either gold, silver, palladium or a platinum electrode material, and the layer of the inert material is a self-assembled monolayer formed onto a surface of the each of the electrodes.

9. A sensor according to claim 1, wherein the voltage power supply is configured to provide a low frequency $f<f_0=100$ Hz signal or DC across said electrodes; and wherein the amplitude of the applied voltage is between 10 mV and 500 mV.

10. A sensor according to claim 1, wherein the conductive particulate material comprises one of a metallic conductor, an inorganic conductor, an organic conductor, or an organic conducting polymer or mixtures thereof.

11. A sensor according to claim 1, wherein said conductive particulate material comprises nanoparticles coated with a non-conductive organic material that is an organic ligand or a mixture of ligands.

12. A sensor according to claim 11, wherein said nanoparticles have diameters less than 100 nm and greater than 2 nm.

13. A sensor according to claim 11, wherein said conductive nanoparticles are made from gold, silver, platinum or palladium.

14. A sensor according to claim 1, wherein said chemiresistor film is an organic conductor with an insulating organic molecule or a polymer or an organic conductive polymer.

15. A method for measuring the presence or amount of an ionic analyte in an electrolyte solution using a sensor according to claim 1, the method comprising:
  (i) contacting the chemiresistive film with an electrolyte solution;
  (ii) applying an electric potential difference between the gate electrode and the chemiresistive film; and
  (iii) measuring a change in the resistance of the chemiresistive film.

16. A method according to claim 15, further comprising the step of comparing a value of the measurement in step (iii) with measurement(s) of the change in the resistance of the chemiresistive film in the presence of said ionic analyte at one or more known concentrations to thereby determine the amount of ionic analyte in said electrolyte solution.

17. A method for modulating the electrical resistance of a chemiresistive film using a sensor according to claim 1, the method comprising:

(i) contacting the chemiresistive film and the gate electrode with an electrolyte solution, wherein at least one component of the electrolyte solution comprises a charged analyte molecule;
(ii) applying an electric potential difference between the gate electrode and the chemiresistive film;
(iii) selectively charging the gate electrode with a net positive charge or a net negative charge; and
(iv) measuring a change in the resistance of the chemiresistive film.

18. A method according to claim 17, wherein the charged analyte molecule comprises one or more positive charges (P) or one or more negative charges (N), wherein the charged analyte molecule has either a net positive charge in the case of (P) or net negative charge in the case of (N), and an interaction group (F) of the following structure: P---F or N---F respectively.

19. A method according to claim 18, wherein the interaction group (F) is (i) an organic functional group which comprises one or more chemical moieties capable of physically or chemically binding to the chemiresistive film; or (ii) contains as part of its structure, a hydrophobic group; or (iii) contains as part of its structure groups capable of forming hydrogen bonds.

* * * * *